(12) United States Patent
Kaplan et al.

(10) Patent No.: US 8,998,927 B2
(45) Date of Patent: *Apr. 7, 2015

(54) MECHANICALLY REGISTERED VIDEOSCOPIC MYRINGOTOMY/TYMPANOSTOMY TUBE PLACEMENT SYSTEM

(75) Inventors: Aaron V. Kaplan, Norwich, VT (US); Joseph Tartaglia, Morgan Hill, CA (US); Robert Vaughan, Stockton, CA (US); Christopher Jones, Sunnyvale, CA (US)

(73) Assignee: Acclarnet, Inc., Menlo Park, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/754,304

(22) Filed: Apr. 5, 2010

(65) Prior Publication Data

US 2010/0256653 A1    Oct. 7, 2010

Related U.S. Application Data

(60) Continuation of application No. 10/841,420, filed on May 6, 2004, now Pat. No. 7,704,259, which is a division of application No. 09/843,541, filed on Apr. 26, 2001, now Pat. No. 6,770,080.

(51) Int. Cl.
*A61F 11/00* (2006.01)

(52) U.S. Cl.
CPC .................................. *A61F 11/002* (2013.01)

(58) Field of Classification Search
CPC ..... A61F 11/00; A61F 11/002; A61F 11/004; A61F 9/00781
USPC ................. 606/109, 108, 185, 196–199, 107; 604/8, 264
See application file for complete search history.

(56) References Cited

U.S. PATENT DOCUMENTS

| 2,162,681 A | 6/1939 | Ryan |
| 3,638,643 A | 2/1972 | Hotchkiss |

(Continued)

FOREIGN PATENT DOCUMENTS

| DE | 199118288 | 10/2000 |
| WO | WO9911175 | 3/1999 |

OTHER PUBLICATIONS

Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.

(Continued)

*Primary Examiner* — Darwin Erezo
*Assistant Examiner* — Lindsey Bachman
(74) *Attorney, Agent, or Firm* — Frost Brown Todd LLC

(57) ABSTRACT

Devices, systems, methods, and kits for treating the tissue structures of the ear make use of a guide structure that can mechanically register a treatment probe with a target region of a target tissue, the guide structure being fittingly received in an auditory canal and often comprising a conformable body such as a compressible foam, or the like. The guide structure may include an articulating mechanism for selectively orienting the treatment probe toward the target region of, for example, a tympanic membrane. The guide structure may also support a videoscopic image capture device, illumination transmitting optical fibers, an aiming beam transmitter, and the like. Such structures facilitate myringotomy, tympanostomy tube placement, and the like, under local anesthesia in a doctor's office.

19 Claims, 16 Drawing Sheets

(56) References Cited

U.S. PATENT DOCUMENTS

| | | | |
|---|---|---|---|
| 3,913,584 A | | 10/1975 | Walchle et al. |
| 4,335,713 A | | 6/1982 | Komiya |
| 4,335,715 A | | 6/1982 | Kirkley |
| 4,380,998 A | * | 4/1983 | Kieffer et al. ............... 600/200 |
| 4,800,876 A | | 1/1989 | Fox et al. |
| 4,913,132 A | | 4/1990 | Gabriel |
| 4,946,440 A | | 8/1990 | Hall |
| 5,026,378 A | * | 6/1991 | Goldsmith, III ............. 606/109 |
| 5,092,837 A | | 3/1992 | Ritch et al. |
| 5,178,623 A | | 1/1993 | Cinberg et al. |
| 5,370,656 A | | 12/1994 | Shevel |
| 5,489,286 A | * | 2/1996 | Cinberg et al. .............. 606/109 |
| 5,496,329 A | * | 3/1996 | Reisinger .................... 606/109 |
| 5,643,280 A | | 7/1997 | Del Rio et al. |
| 5,658,235 A | | 8/1997 | Priest et al. |
| 5,676,635 A | | 10/1997 | Levin |
| 5,681,323 A | * | 10/1997 | Arick ........................... 606/108 |
| 5,775,336 A | | 7/1998 | Morris |
| 5,827,295 A | | 10/1998 | Del Rio et al. |
| 5,893,828 A | | 4/1999 | Uram |
| 5,893,837 A | | 4/1999 | Eagles et al. |
| 5,984,930 A | | 11/1999 | Maciunas et al. |
| 6,022,342 A | | 2/2000 | Mukherjee |
| 6,045,528 A | * | 4/2000 | Arenberg et al. ............... 604/28 |
| 6,110,196 A | | 8/2000 | Edwards |
| 6,171,236 B1 | | 1/2001 | Bonutti |
| 6,398,758 B1 | * | 6/2002 | Jacobsen et al. ............. 604/104 |
| 6,440,102 B1 | * | 8/2002 | Arenberg et al. .......... 604/96.01 |
| 6,447,522 B2 | * | 9/2002 | Gambale et al. ............. 606/108 |
| 6,475,138 B1 | * | 11/2002 | Schechter et al. ........... 600/108 |

OTHER PUBLICATIONS

Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).

Lindeman et al., The "Arrow Tube" Residents in Otolaryngology, Massachusetts Eye and Ear Infirmary, 1 page total (1964).

Pappas, "Middle Ear Ventilation Tubes" Meeting of the Southern Section of the American Laryngological, Rhinological and Otological Society, Inc., Williamsburg, VA, Jan. 12, 1974, pp. 1098-1117.

Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.

Reuter,. "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.

Ringenberg, "A New Middle Ear Ventilation Device" Seventy-second Annual Session of the American Academy of Ophthalmology and Otolaryngology, Oct. 29-Nov. 3, 1967, Chicago, IL, 1 page total.

Schmidt et al. "Transtympanic Aeration of the Middle Ear With Blocked Eustachian Tube" Acta Otolaryng., pp. 277-282 (1965).

Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.

Santa Barbara Medco, Inc. "Otological Ventilation Tubes" Product Brochure from http://www.sbmedco.com/ptfe_shepard.asp, 8 pages total. (Feb. 11, 2001).

* cited by examiner

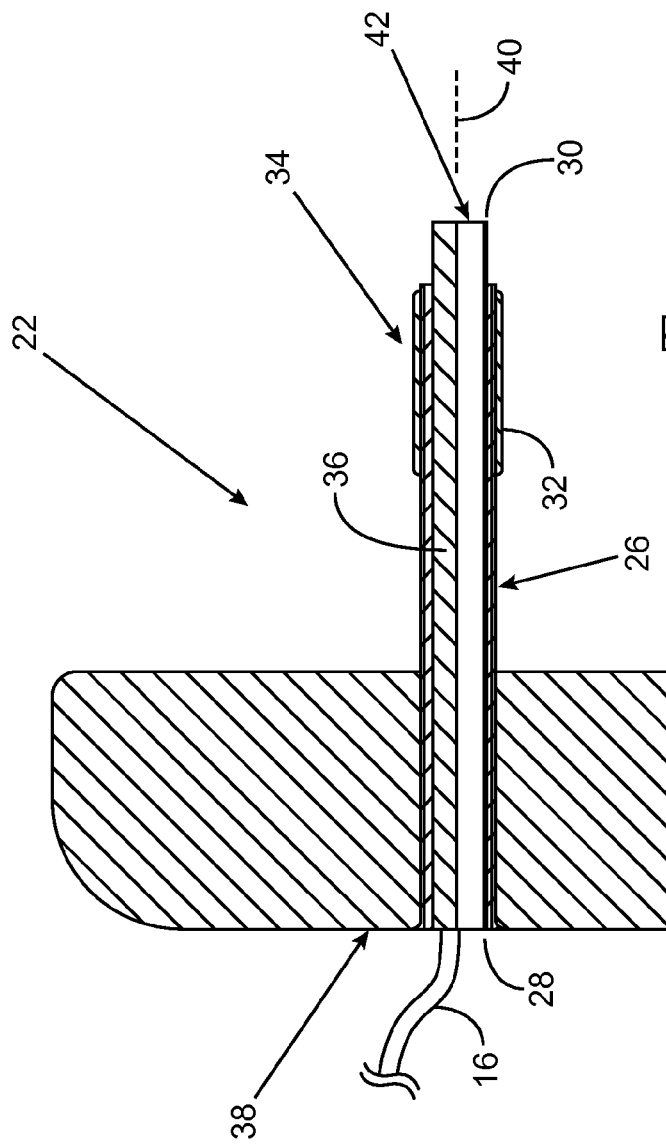
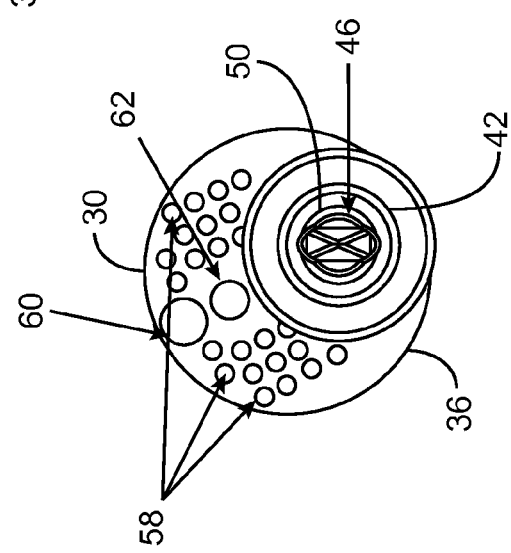
FIG. 4
FIG. 3

FIG. 9G   FIG. 9F   FIG. 9E   FIG. 9D   FIG. 9A
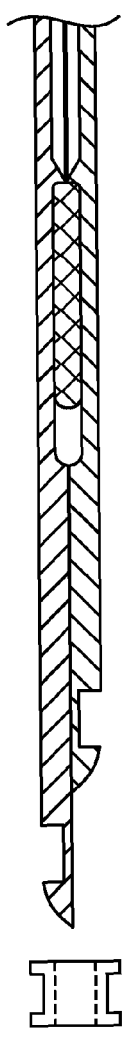
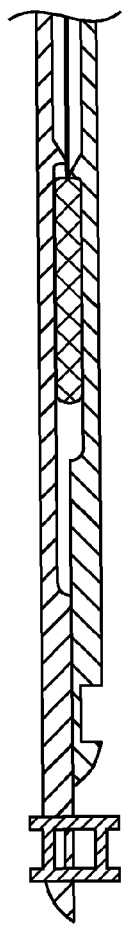
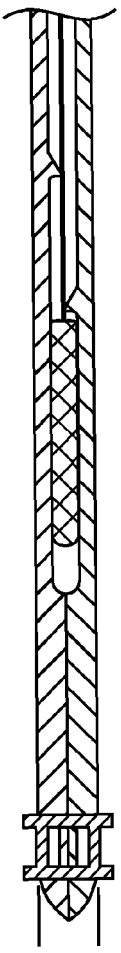
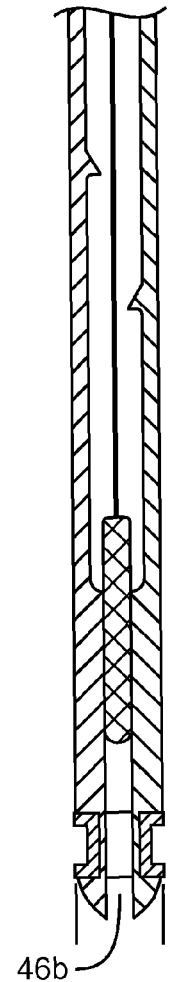
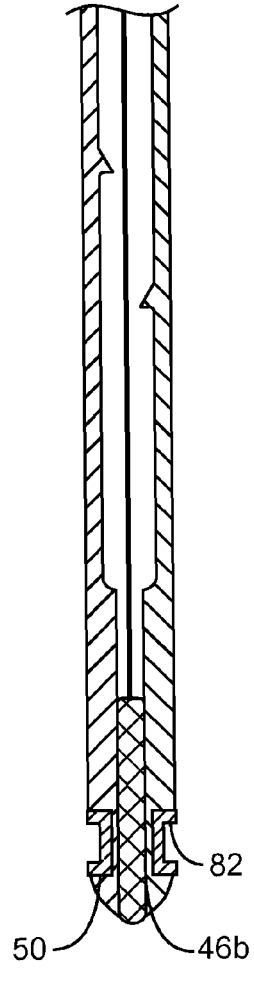
FIG. 9B
FIG. 9C
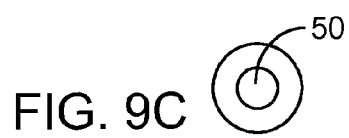

MECHANICALLY REGISTERED VIDEOSCOPIC MYRINGOTOMY/TYMPANOSTOMY TUBE PLACEMENT SYSTEM

CROSS-REFERENCE TO RELATED APPLICATION

This patent application is a continuation of U.S. patent application Ser. No. 10/841,420 filed May 6, 2004, now U.S. Pat. No. 7,704,259, which is a divisional application which claims priority from U.S. patent application Ser. No. 09/843,541 filed Apr. 26, 2001, now U.S. Pat. No. 6,770,080, the full disclosures of which are incorporated herein by reference.

BACKGROUND OF THE INVENTION

The present invention is generally related to medical devices and apparatus. In particular, the invention provides systems, methods, devices, and kits for treating a patient's ear. In one embodiment, the invention provides a system and method for myringotomy with or without tympanostomy tube placement.

Otitis media is among the most common diagnosis made by pediatricians. A majority of children may have at least one episode of otitis media ("earache") prior to their third birthday. Otitis media is often caused by an inability of the eustachian tube to drain fluid from the middle ear. Otitis media is often treated with antibiotics.

A significant number of children exhibit recurrent episodes of otitis media and/or otitis media with effusion. Treatment of these more severe cases often involves the placement of a tympanostomy tube through the tympanic membrane so as to provide adequate drainage of the middle ear and reduce the likelihood of future infections. Tympanostomy tubes provide fluid communication between the middle and outer ear, and typically fall out spontaneously within about a year of placement. Tympanostomy tube placement is among the most common surgical procedures performed in the pediatric population. It has been estimated that more than a million tympanostomy tubes may be placed each year, with typical patients being between about 18 months and 3 years of age at the time of the procedure.

Tympanostomy tube placement is typically performed in an out-patient surgery setting under general anesthesia. The external auditory canal and tympanic membrane are examined under microscopic visualization through a hand-held conical shaped speculum. An incision or myringotomy is made in the tympanic membrane, typically using an elongate, small profile scalpel which the physician extends through the conical speculum. Fluid may be aspirated through the myringotomy, and a tympanostomy tube is placed so as to extend through the tympanic membrane.

A wide variety of tympanostomy tubes are commercially available, and a still wider variety of others tubes have been proposed. A number of systems have been proposed to both perform the myringotomy and deploy the tympanostomy tube with a single treatment assembly. In recent years, more complex and expensive systems have been proposed for diagnosis or treatment of the tissues of the ear, including systems using laser energy for forming a myringotomy, video systems for imaging of the ear canal, and the like. These various alternatives have, not surprisingly, been met with varying degrees of acceptance.

A standard tympanostomy tube placement procedure is both effective and quite safe. Nonetheless, further improvements would be desirable. In particular, there are both risks and costs associated with out-patient surgical procedures performed under general anesthesia. For example, a significant portion of the risk and cost of tympanostomy tube placement is associated with the administration of general anesthesia, i.e., the need for an operating room, the presence of an anesthesiologist, and related recovery room time.

In light of the above, it would be desirable to provide improved devices, systems, methods, and kits for treatment of the tissue structures within the auditory canal. It would generally be beneficial if these improvements facilitated myringotomy with or without tympanostomy tube placement without having to resort to general anesthesia, thereby allowing these common procedures to be performed in a doctor's office (rather than in an outpatient surgical facility). It would be further beneficial to maintain or enhance the physician's control over the procedure by, for example, allowing verification of intended and actual tympanostomy tube placement location, enhanced viewing and control, and improved safety. It would further be desirable if these improvements could be provided while decreasing the overall procedure time, and ideally, at a reduced overall procedure cost.

SUMMARY OF THE INVENTION

The present invention provides improved devices, systems, methods, and kits for treating the tissue structures of the ear. The invention often makes use of a guide structure that can mechanically register a treatment probe with a target region of the tympanic membrane or eardrum. Mechanical registration may be provided by a structure which is fittingly received in an external auditory canal of the ear. The guide structure will often include a conformable body (typically comprising a compressible foam, or the like) so as to allow the guide structure to accommodate a range of differing auditory canal anatomy. The guide structure may further include an articulating mechanism for selectively orienting the treatment probe toward the target region of the tympanic membrane. The articulating mechanism will often selectively orient a probe lumen, with the treatment probe having a shaft fittingly sliding in the probe lumen so that engagement between a positioning surface of the guide structure and a tissue surface of the patient's ear maintains registration of the treatment probe. The guide structure may also support a videoscopic image capture device, illumination transmitting optical fibers, an aiming beam transmitter, and the like. Advantageously, such structures facilitate performing treatment procedures such as myringotomy, tympanostomy tube placement, and the like, under local (rather than general) anesthesia, often in a doctor's office (rather than an out-patient surgical facility).

In a first aspect, the invention provides a method for treating an ear of a patient. The ear has a tympanic membrane. The method comprise mechanically registering a guide structure with a target region of the tympanic membrane. The target region is treated by actuating a treatment probe while the treatment probe is oriented by the registered guide structure.

Orientational alignment between the guide structure and the tympanic membrane may be maintained by engagement between a surface of the guide structure and an external auditory canal. This engagement may be sufficient to maintain orientation of the treatment probe without manual support of the guide structure or treatment probe. The use of a conformable body of the guide structure can facilitate the orientation maintaining engagement. The conformable body may comprise a compressible foam, a solid elastomer, a balloon, or the like, and may optionally expand radially within the auditory canal. An agent (such as a local anesthesia agent, an antiseptic agent, an antibiotic agent, or the like) may be dispensed from the guide structure, the agent optionally being dispensed from the compressible foam. In alternative embodiments, one or more such agents may be dispensed before insertion of the guide structure and/or after its removal. In some embodiments, registration of the probe and target region may be provided at least in part by engagement (preferable in the form of gentle pressure) between the guide structure and the skull (often the side of the skull) of the patient.

The guide structure may be registered by articulating a treatment lumen of the guide structure relative to a positioning surface of the guide structure. For example, the guide structure may comprise a shaft eccentrically carrying the treatment lumen. The shaft may rotate within the auditory canal about an axis with the treatment probe precessing about the axis so as to orient the probe toward the target region. The positioning surface of the guide structure may be disposed over the shaft with a bearing therebetween to facilitate rotation without injury to the tissue surface engaged by the positioning surface. The shaft may flex during rotation so as to accommodate a bend of the auditory canal. The probe and/or other components of the treatment system within the guide structure may likewise flex during rotation.

Registration of the guide structure may be videoscopically directed, the guide structure optionally supporting a video image capture device. The tympanic membrane may be illuminated by the guide structure, typically using an illumination source and/or optics (such as a fiber optic bundle, glass rod, or other optical waveguide). The registration of the probe with the target region may optionally be verified by displaying a marker indicating which portion of the tympanic membrane is aligned with the probe. For example, an aiming beam may be transmitted onto the tympanic membrane from the guide structure to generate the marker or pointer. The aiming beam may comprise, for example, laser light energy having a frequency within the visible range. In some embodiments, a reticule or image template may be superimposed on the image displayed to the system operator to aid registration.

A system operator disposed in front of the patient may view an image of the tympanic membrane while a head of the patient is upright. The system operator may manipulate a handle coupled to the shaft of the guide structure to register the guide structure and actuate the treatment probe. In the exemplary embodiment, the guide structure handle is a large profile body, similar in appearance to an earmuff when in use. The system of the present invention is particularly well-suited for tympanostomy tube placement without general anesthesia.

The treatment probe will typically pierce the tympanic membrane. A tympanostomy tube may be advanced through the pierced membrane, often while supporting the tympanostomy tube with the guide structure. The treatment probe may carry the tympanostomy tube. Alternatively, separate probes may be used to pierce the membrane and deploy the tympanostomy tube. In still further alternatives, the membrane may be pierced using laser energy or the like. Fluid may be drained from distally of the pierced membrane by the treatment probe, by a separate aspiration structure supported by the guide structure, or the like. Fluid drainage may be effected by an aspiration lumen, by an absorbent structure such as a blotting or wicking element, or the like.

In another aspect, the invention provides a system for treating an ear of a patient. The ear has a tympanic membrane and a tissue surface. The system comprises a guide structure having a proximal orientation and a distal orientation. The guide structure has a positioning surface. A tympanic membrane treatment probe is oriented by the guide structure. The guide structure maintains registration of the treatment probe with a target region of the tympanic membrane when the positioning surface engages the tissue surface of the ear.

The tissue surface typically comprises an auditory canal. The guide structure will often include a conformable body insertable into the auditory canal. A shaft may be rotatably disposed within the conformable body so as to rotate about an axis. The treatment probe can be oriented eccentrically relative to the axis so that rotation of the shaft selectively registers the treatment probe with the target region. The shaft may be laterally flexible to conform with a bend of the auditory canal during rotation of the shaft. Similarly, the treatment probe may also be flexible.

The conformable body may comprise a compressible material such as a foam. In some embodiments, an agent such as a local anesthetic agent, an antiseptic and/or antibacterial agent, an antibiotic agent, and/or the like may be disposed on or in the foam, or the agent may otherwise be dispensed from the guide structure. The guide structure may further include one or more aspiration and/or irrigation lumens, or such lumens may alternatively be incorporated into the treatment probe. Such aspiration and/or irrigation may be used to clear Cerumen (earwax) for imaging of the tympanic membrane, fluid accumulating distally of the tympanic membrane, and the like.

An image capture device may be supported by the guide structure for imaging the tympanic membrane. The image capture device may coupled to a monitor, the image capture device typically comprising a Charge-Coupled Device (CCD) and associated imaging optics (such as a coherent fiber optic bundle, one or more rod or standard lenses, and the like). At least a portion of the image capture device may be removably couplable to the guide structure, which may allow the use of disposable guide structures at a reasonable cost. An illumination source may also be carried on the guide structures for illuminating the tympanic membrane during imaging. The exemplary illumination source may comprise illumination optical fibers.

The system will preferably include aiming means for identifying an orientation of the treatment probe relative to the tympanic membrane. In many embodiments, a light beam (such as from a laser or light-emitting diode) may be directed onto the tympanic membrane at a location aligned with the treatment probe. Alternative embodiments may make use of a reticule superimposed on the image of the tympanic membrane as shown in a monitor to the system operator, a template superimposed on the image to indicate the target region, or the like. Such aiming structures can verify registration of the treatment probe with the target region before, during, and/or after piercing the tympanic membrane, tube deployment, and the like.

The treatment probe will often have a distal tip for piercing the tympanic membrane. Optionally, the distal tip may comprise a cutting edge or blade. A tympanostomy tube may be releasably carried on a shaft of the probe proximally of the tip. An exemplary tympanostomy tube comprises a proximal flange and a distal flange with a tubular body therebetween, the tubular body having an elongate opening with a first cross-sectional dimension and a second cross-sectional dimension greater than the first. The tip of the probe shaft may have a distal edge oriented along the height when the tympanostomy tube is carried on the shaft. The distal surface of the distal flange of the tympanostomy tube may angle proximally and radially outwardly to facilitate advancing the distal flange through the myringotomy.

A limit surface of the treatment probe may engage a limit surface of the guide structure or the tympanic membrane so as to inhibit axial movement of the shaft after the probe pierces the tympanic membrane. This can help avoid inadvertent injury to the middle and/or inner ear structures or undesired positioning of the tube distally of the tympanic membrane within the middle ear. In the exemplary embodiment, engagement of the limit surfaces inhibits movement when the distal end of the probe advances from the guide structure by a distance in a range from about 1.0 mm to about 40 mm.

The treatment probe may comprise a probe shaft disposed in a lumen of the guide structure. The probe shaft may be coupled to an actuator which is accessible when the positioned surface engages the tissue surface. The probe shaft may advance axially with the lumen in response to movement of the actuator. The lumen may be selectively repositionable relative to the positioning surface for selective registration of the treatment probe with the target region. for example, the lumen may be supported by a shaft which rotates relative to the positioning surface, with the lumen being eccentrically oriented and/or eccentrically disposed relative to the axis of rotation of the shaft.

BRIEF DESCRIPTION OF THE DRAWINGS

FIG. 3 is an axial view of the distal end portion of the guide structure and treatment probe of FIG. 2.

FIG. 4 is a cross-sectional view of the guide structure.

FIGS. 9A-9G schematically illustrate an alternative treatment probe for use in the system of FIG. 1.

DETAILED DESCRIPTION OF THE INVENTION

The present invention generally provides improved devices, systems, methods, and kits for treatment of tissue structures of the ear. Myringotomy, tympanostomy tube placement, and other procedures may be performed using a guide structure to register one or more treatment probes relative to the target tissue structure. The guide structure will often be articulatable, allowing selective registration of the treatment probe with a target region of, for example, the tympanic membrane or eardrum. The guide structure may be supported by, for example, a conformable body, such as a compressible foam insertable into the external auditory canal. Engagement between the conformable body and the auditory canal can maintain a position of the guide structure so that the guide structure, in turn, maintains an orientation of the treatment probe. Such a lightweight guide structure may be mountable to the patient, allowing stabilized videoscopic imaging from an image capture device supported by the guide structure. Illumination transmitting optical fibers, an aiming beam transmitter, aspiration/irrigation lumens, and other structures may be supported by a single guide structure. Advantageously, such a stabilized system facilitates performing treatment procedures such as myringotomy with or without tympanostomy tube placement, and the like, under local (rather than general) anesthesia, often in a doctor's office (rather than an operating room).

The structures and methods of the present invention will be particularly useful for accessing and treating the tissue structures of the ear. Using an image capture device which is supported by a guide structure affixable relative to an adjacent tissue surface of the ear, the images of these small tissue structures will remain steady despite movements of the patient's head. A magnified scale of the image may greatly ease viewing of the target tissues, and as the treatment probe can also be supported by the guide structure, procedures may be directed with reference to an enlarged, stabilized image shown in a monitor, with much greater precision than a manual procedure performed under direct optical imaging. Hence, while the invention may find its most immediate application in formation of myringotomies with or without tympanostomy tube placement, and the like, the invention may find further applications in a number of applications of the outer, middle, and or inner ear, including cerumen removal, tympanocentesis, foreign body removal, ear implants, and the like.

Figure 1:
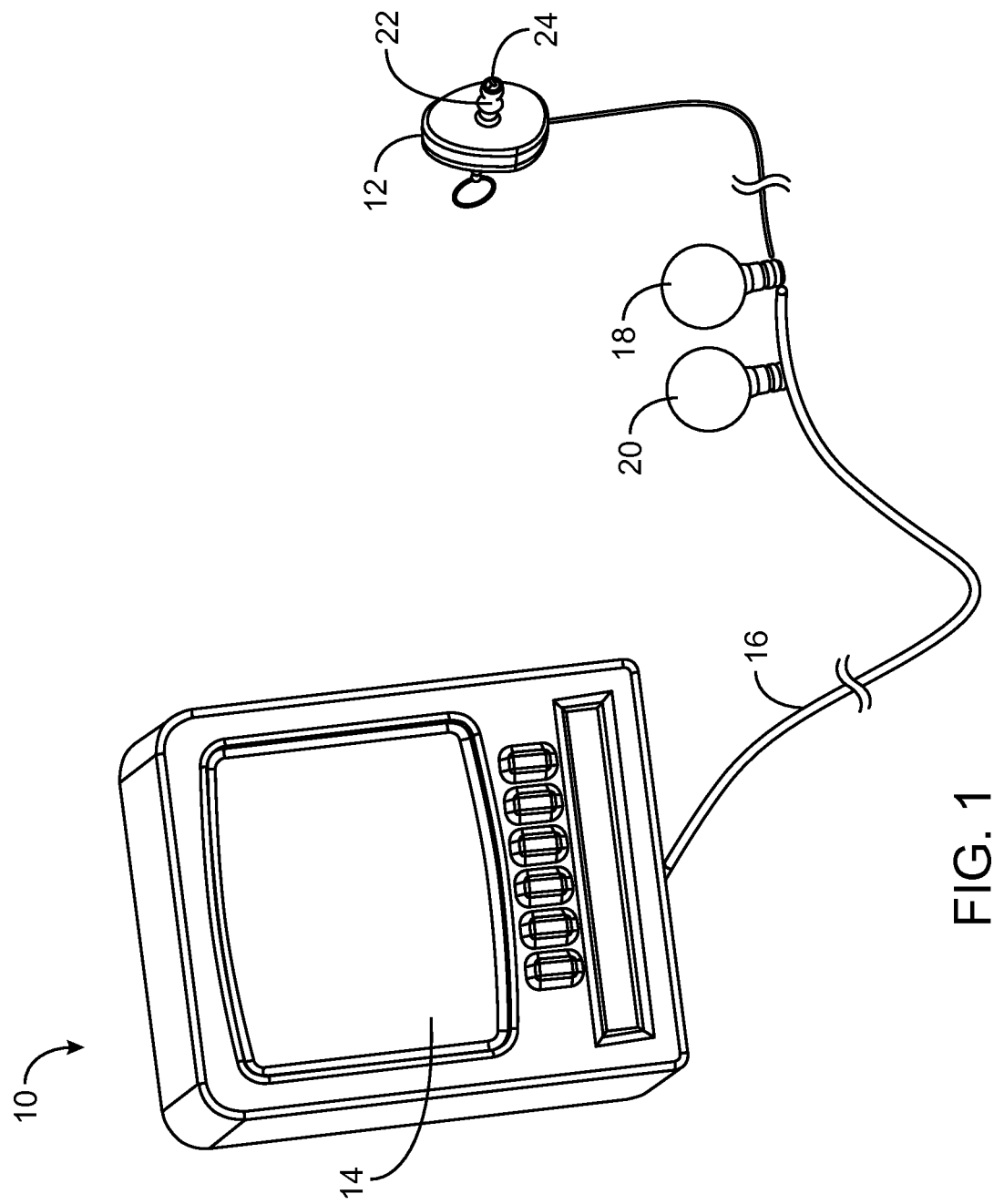
FIG. 1 schematically illustrates a tympanic membrane treating system.

Referring now to FIG. 1, a tympanostomy tube placement system 10 comprises a probe assembly 12 coupled to a video monitor 14 by an image transmission cable 16. An illumination light source 18 (shown schematically) transmits illumination light to probe assembly 12 for use in imaging, and an aiming light source 20 (also shown schematically) transmits a pointer light beam to the probe assembly for registering the probe assembly with a target tissue. An optical image of the auditory canal and tympanic membrane may be transmitted from probe assembly 12 to a camera 19 (shown schematically), which transforms the optical image into image data in a form convenient for transmission, recording and/or manipulation (the camera typically comprising a charge-coupled device or "CCD"). This image data is transmitted by camera 19 to monitor 14, again via cable 16. Monitor 14 will often comprise a standard video display, optionally being part of a display rack system modified for use in system 10. The rack may incorporate the illumination and/or aiming light sources 18, 20, camera 19, an image storage unit 15 (such as a videocassette recorder, CD or DVD recorder, or the like), a printer, and/or the like. Suitable video rack systems may be commercially available from STRYKER, located at Santa Clara, Calif.

Illumination source 18 will generally comprise an incandescent lamp, fluorescent or arc lamp, light emitting diode, or the like, and will often be optically coupled to illuminating optical fibers of cable 16 so as to transmit white imaging light to probe assembly 12. In other embodiments, alternative illumination frequencies and/or sources might be used, ambient light may be sufficient, or non-optical imaging might be applied. Aiming light source 20 may comprise a laser or light emitting diode (or the like) transmitting a light beam with a frequency in the visible spectrum (such as a green light beam, a red light beam, or the like). The aiming light beam will often be transmitted to probe assembly 12 via dedicated optical fibers of cable 16 for directing of an aiming or pointer beam onto the target tissues so as to generate an aiming marker. Image transmission cable 16 may further comprise a coherent fiber optic bundle (particularly for transmission of an image from probe assembly 12 to camera 19), a coaxial electrical cable (particularly for transmission of image date from camera 19 to monitor 14), one or more data transmission optical fibers, and/or the like, and generally transmits an image from probe assembly 12 to monitor 14 for use in videoscopically directing a tympanostomy tube placement procedure. Cable 16 may also have an aspiration and/or irrigation lumen, or one or more separate fluid tubes may optionally be coupled to probe assembly 12 for clearing of cerumen to enhance image quality, aspirating fluids from the middle ear, or the like. Optionally, agents such as antibiotic, antibacterial, cerumenolytics, and/or local anesthetic agents may be included (alone or in combination) with irrigation flow. Suitable local anesthetic agents include lidocaine, bupivacaine, benzocaine, prilocaine, lidocaine/prilocaine in a eutectic mixture, tetracaine, and the like. Suitable antibiotics include neomycin, polymixin B, ciprofloxacin, ofloxin, and the like. Suitable cerumenolytics may include Triethanolamine polypeptide oleatecondensate, hydrogen peroxide, and the like. suitable antibacterial agents include aqueous aluminum acetate, acetic acid, and the like.

Referring now to FIGS. 1-4, treatment probe assembly 12 generally includes a guide structure 22 and a treatment probe 24. Guide structure 22 generally includes a shaft 26 having a proximal end 28 and a distal end 30, at least a portion of the shaft adjacent distal end 30 being safely insertable into an external auditory canal of the patient. A positioning surface 32 disposed about the shaft 26 is defined by a conformable body 34.

Conformable body 34 may comprise a compressible foam, and will preferably comprise a urethane foam. Alternatively, conformable body 34 may comprise a material such as gum rubber compounds, urethanes, fluorocarbon elastomer, butyl rubber, EPDM (Ethylene-Propylene Rubber), latex rubber, neoprene (polychloroprene), nitrile rubber (acrylonitrile), polybutadiene, silicone rubber, SBR (Stryrene-Butadiene Rubber), HNBR (Hydrogenated Nitrile Rubber), fluoroelastomer, fluorosilicone. Conformable body 34 can safely engage the surrounding auditory canal with sufficient force and/or friction to inhibit movement of the guide structure during imaging and treatment. Conformable body 34 may expand resiliently within the external auditory canal, or the conformable body may comprise a selectably expandable body such as a balloon. In other embodiments, conformable body 34 may comprise a soft solid elastomer, a plastically deformable polymer, or the like.

Figure 2:
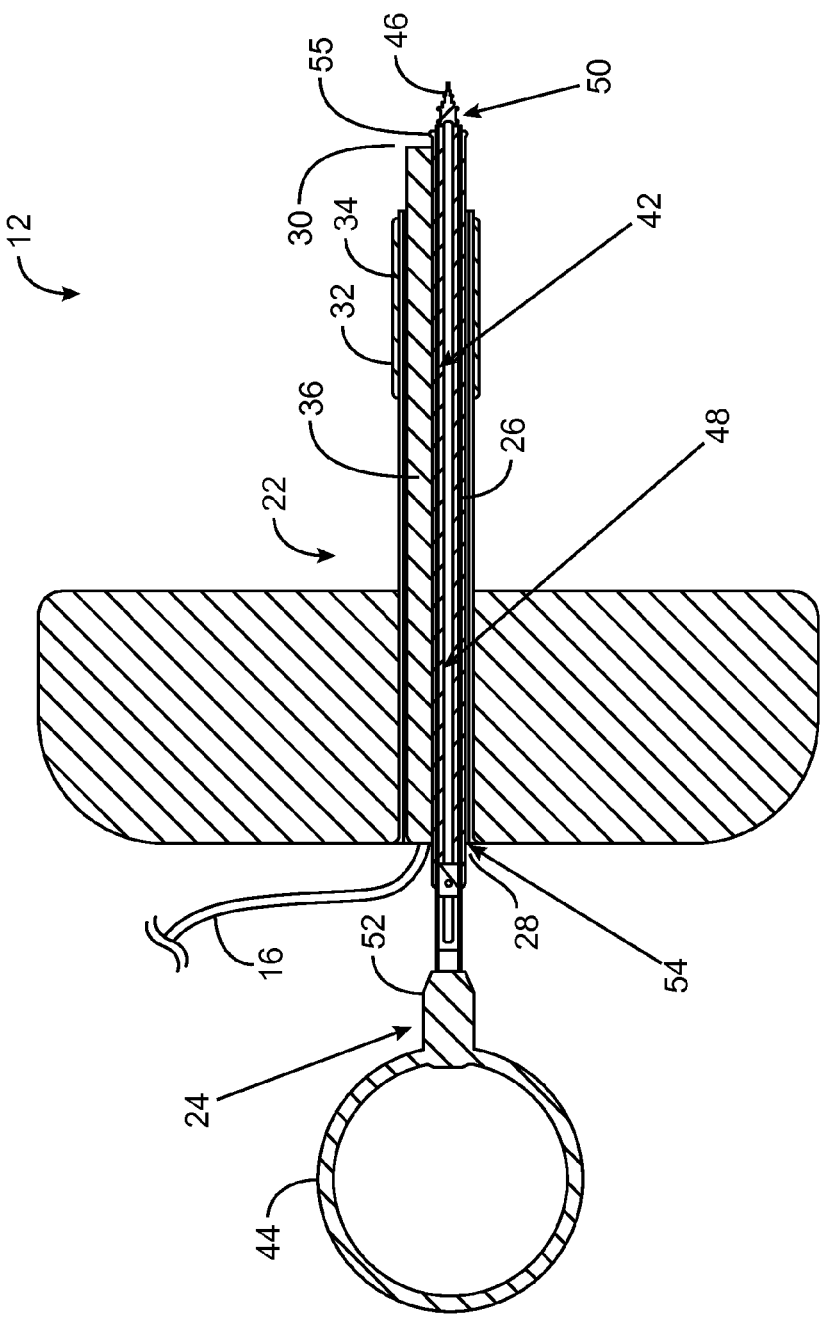
FIG. 2 is a cross-sectional view of a guide structure and myringotomy/tympanostomy probe for use in the system of FIG. 1.

An inner shaft 36 is rotatably disposed within conformable body 34, as can be seen in FIGS. 2 and 4, and is rotatably coupled to a proximal handle 38. Inner shaft 36 rotates about an axis 40, and has a probe lumen 42 which is eccentric relative to axis 40. Hence, by rotating proximal handle 38, the system user can selectively reposition probe lumen 42 relative to positioning surface 32, and to the patient's tissues. This provides a simple mechanism to allow selective registration of probe 24 with a target tissue of the tympanic membrane. In the exemplary embodiment, the engaging surfaces of inner shaft 36 and rotatable body 34 define a rotational bearing 35 to accommodate rotational repositioning of inner shaft 36 relative to the conformable body, thereby avoiding an injury to the engaged tissue surface when the probe is moved. Optionally, a releasable rotational lock may inhibit inadvertent rotational movement of the inner shaft relative to the conformable body so as to avoid loss of registration. Alternatively, rotational friction of bearing 35 may be sufficient to maintain registration, while still allowing manual movement of inner shaft 36 by manual manipulation of handle 38. Axial displacement of rotatable conformable body 34 may be inhibited, optionally by engagement between a surface of the conformable body and a surface of one or more axial restraining elements 37. Restraining elements 37 may be disposed proximally and/or distally of conformable body 34.

A variety of alternative articulatable mechanisms may be included to allow selective repositioning of probe lumen 42 relative to positioning surface 32 in probe assembly 12. In some embodiments, one or more selectively expandable structure (such as angioplasty-like balloons) may be eccentrically disposed about a probe lumen tube within an outer sheath, so that selective expansion of the eccentric structure(s) laterally repositions the probe lumen. More complex eccentric rotation mechanisms may vary the lateral offset of the lumen from shaft axis 40. For example, an intermediate eccentric shaft may be disposed between and selectively rotatable relative to eccentric inner shaft 36 and to an outer sheath. Alignment of the offset of the inner and intermediate eccentric shafts could move the probe lumen farther away from axis 40, while counteracting the eccentricity of inner shaft 36 with that of the intermediate shaft would move the probe lumen closer to axis 40. Still further alternatives are possible, including axial sliding probe lumen supports which vary an eccentric angle of probe lumen 42 relative to axis 40 adjacent distal end 30, steerable articulating probes which can be selectively laterally offset from an axis of the probe lumen 42, and the like.

In the exemplary embodiment, handle 38 of guide structure 22 comprises a body having a larger profile than shaft 26 for selective manual rotation of the inner shaft. Handle 38 (and probe assembly 12 in general) may have an appearance similar to a single earmuff when in use, or a pair of probe assemblies may be coupled together by a headband, giving the appearance of headphones or a helmet. Alternatively, a single probe assembly may be coupled to a headband. Optionally, a noise transmitter may be supported by guide structure 22 to transmit music, white noise, or the like, during treatment with the probe 24. This may help to mask the mechanically transmitted sound perceived by a patient when tool 24 pierces (or otherwise treats) a tympanic membrane, for example. In combination with local anesthesia to inhibit pain, such a masking noise transmitter might avoid alarming pediatric patients who are awake during a tympanostomy tube placement procedure.

Referring to FIGS. 2 and 3, treatment probe 24 generally has a proximal actuation handle 44, a distal membrane piercing tip 46, and a probe shaft 48 therebetween. Probe 24 releasably carries a tympanostomy tube 50 proximally of probe tip 46, the exemplary probe being used to both form the myringotomy and to deploy the tympanostomy tube through the pierced membrane. Shaft 48 slides fittingly in probe lumen 42, so that probe 24 is oriented by the guide structure 22, and actuation of probe handle 44 by moving the probe handle toward the guide structure advances the probe tip 46 and tympanostomy tube 50. Engagement between a distal surface 52 of actuation handle 44 and a proximal surface 54 of guide structure 22 limits the axial travel of the probe within the guide structure to inhibit inadvertent injury of the tissue structures of the middle or inner ear. Alternatively, a flange 55 of probe 24 adjacent tip 46 may engage the surface of the tympanic membrane to limit distal travel of the probe. Probe tip 46 and tympanostomy tube 50 may optionally be retractable into and/or through probe lumen 42 to help avoid injury during insertion of shaft 26 into the external auditory canal. Probe shaft 48 and surrounding guide structure shaft 26 may be flexible to accommodate bends of the auditory canal. The exemplary probe will have sufficient column strength adjacent tip 46 for penetrating the tympanic membrane. In the exemplary embodiment, treatment probe 24 comprises solid cylindrical shaft.

Referring to FIG. 3, the eccentric location of probe lumen 42 within outer shaft 36 can be clearly seen in this end view. An illumination light transmitter 58 is shown as a plurality of waveguides or fiber bundles, but may alternatively comprise a single waveguide or bundle. An imaging lens end 60 is also shown, as well as an aiming light transmitter 62. As described above, optical fibers or other transmission means may transmit imaging light via probe assembly 12 for imaging the structures of the ear. An aiming light beam may be transmitted from aiming light transmitter 62, with the aiming beam acting as a light pointer to indicate the alignment of the probe. Optionally, illumination and aiming light may be generated locally at the probe assembly using light emitting diodes, laser diodes, or the like. The aiming beam and the probe may be angled so that the aiming light beam forms a light spot at the portion of the tympanic membrane toward which the probe is aligned. This may be accomplished by angling the aiming beam and/or probe lumen adjacent distal end 30. The distance between the guide structure and the tympanic membrane may be determined by focus of the imaging system, by focus of the aiming beam, by intersection of a plurality of aiming beams, or the like. Alternatively, the aiming beam and probe may be aligned by inserting an aiming beam transmitter into the probe lumen to verify orientation of the probe lumen, and then replacing the aiming beam transmitter with the probe. Aspiration and/or irrigation may be provided by one or more lumens 97 of the guide structure 22 or of probe 24.

Figure 5C:
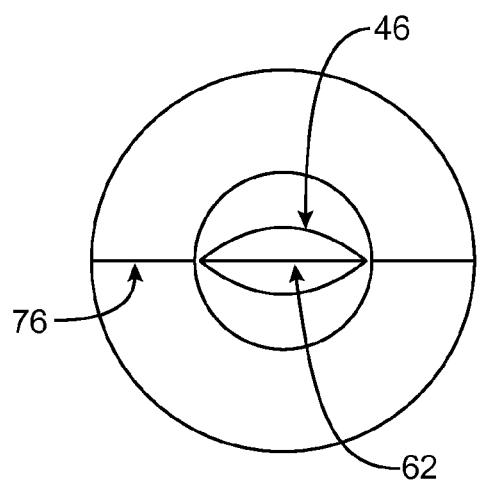
FIGS. 5A-5F are front, side, and end views of a distal portion of the treatment probe, showing an exemplary tympanostomy tube carried thereon.
Figure 5B:
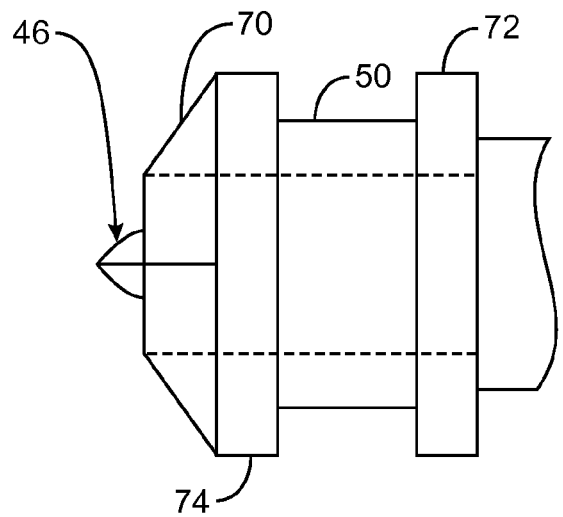
Figure 5A:
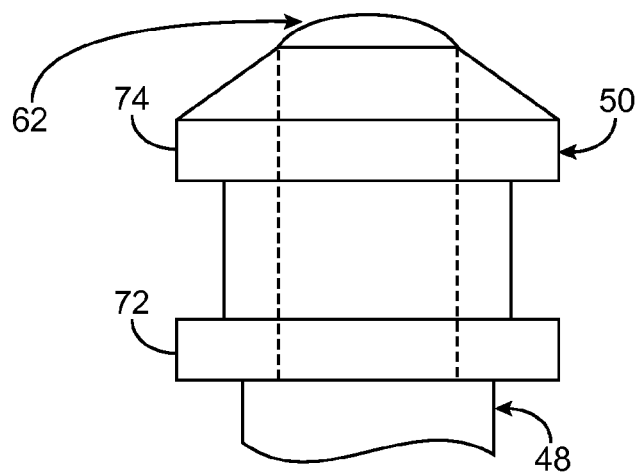
Figure 5F:
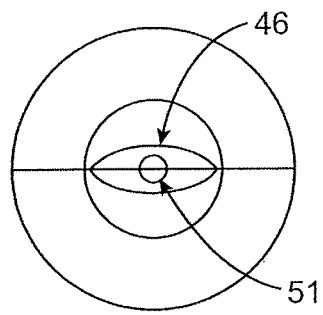
Figure 5E:
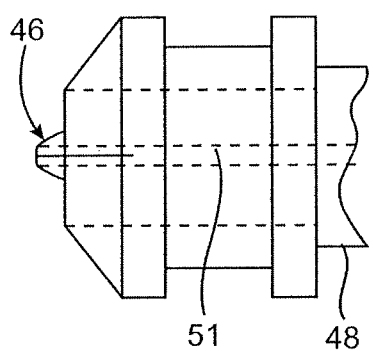
Figure 5D:
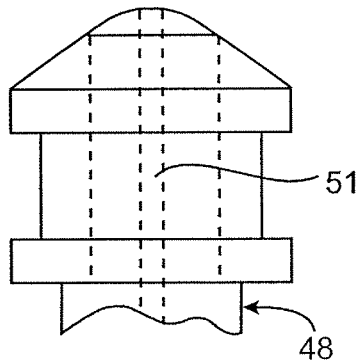
Figure 7:
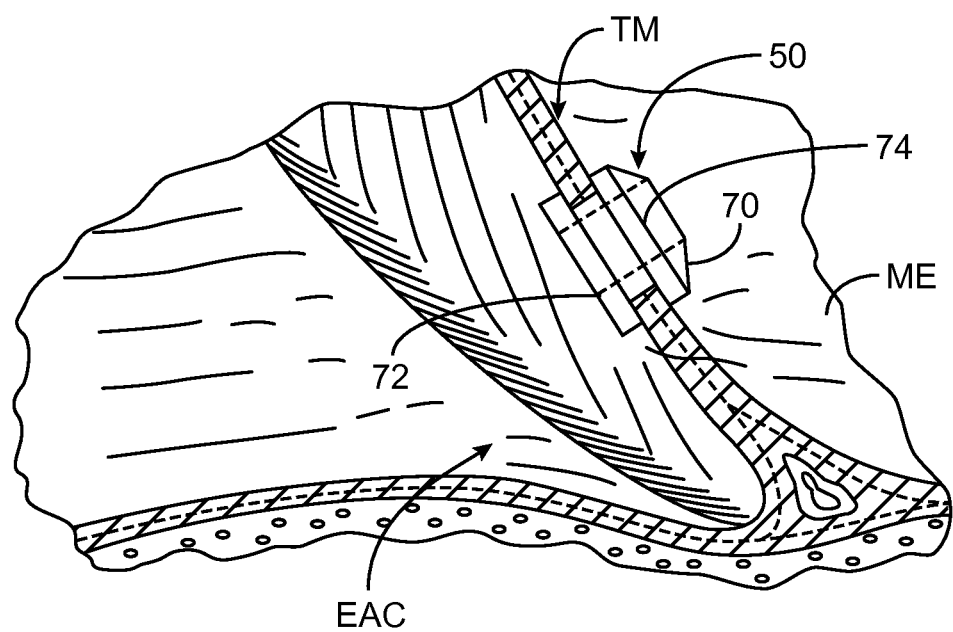
FIG. 7 schematically illustrates the tympanostomy tube of FIG. 6 deployed through the tympanic membrane.
Figure 6:
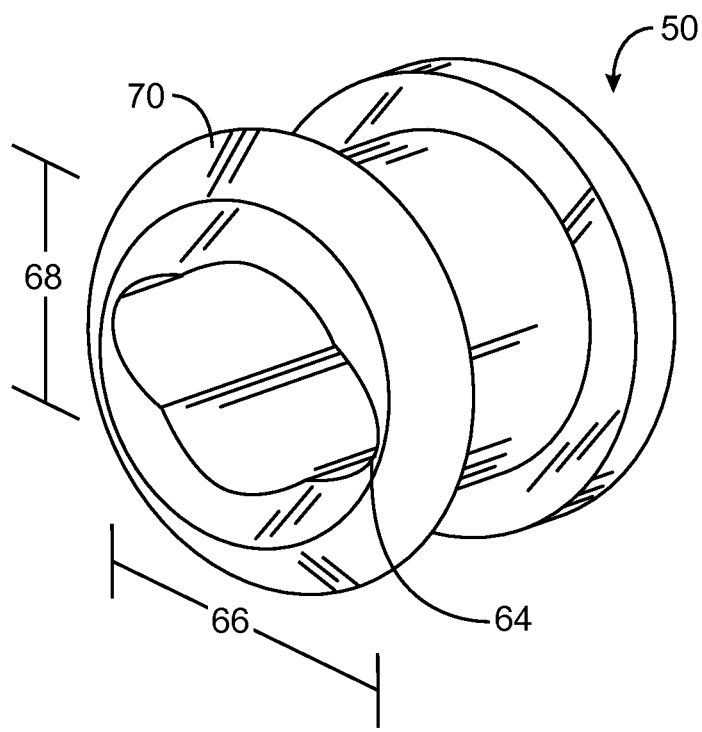
FIG. 6 is a perspective view of an exemplary tympanostomy tube.

An exemplary probe tip 46 and tympanostomy tube 50 are illustrated in FIGS. 5A-6, while a tube deployed through a tympanic membrane TM is illustrated in FIG. 7. Probe tip 46 includes a distally oriented cutting edge 62, which will often be surgically sharp. The associated tube has an opening 64 with a first cross-sectional dimension 66 and a second cross-sectional dimension 68 that is much smaller than the first, so that the length of the cutting member is aligned with the elongate opening. Tube 50 has a proximal flange 72 and a distal flange 74 to help hold the tube in position through tympanic membrane TM, so that the tube extends from an external auditory canal EAC to a middle ear ME. A distal surface of distal flange 70 angles radially outwardly and proximally to facilitate advancing the probe and tube through the tympanic membrane, the distal surface of the tube often being contiguous and/or conformal with the distal surface of the probe tip. Optionally, there may be a distally oriented edge 76 on flange 70, this edge of the tube acting as an extension of the cutting blade edge to help push the distal flange through the membrane TM. The exemplary tympanostomy tube 50 comprises a biocompatible material such as stainless steel, silicone, PTFE, and the like. Another probe system (and the method for its use) which may be used with the guide systems and methods of the present invention is described in U.S. Pat. No. 5,026,378, entitled "Punch Myringotomy System and Method," the full disclosure of which is incorporated herein by reference.

Figure 8A:
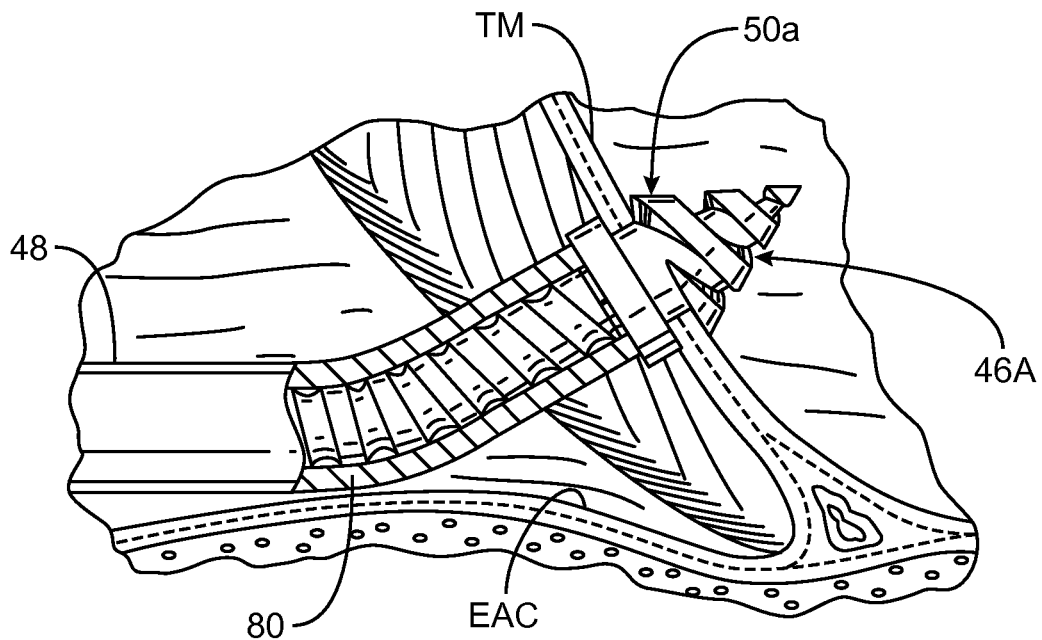
FIGS. 8A and 8B illustrate an alternative tympanostomy tube and treatment probe for use in the system of FIG. 1.
Figure 8B:
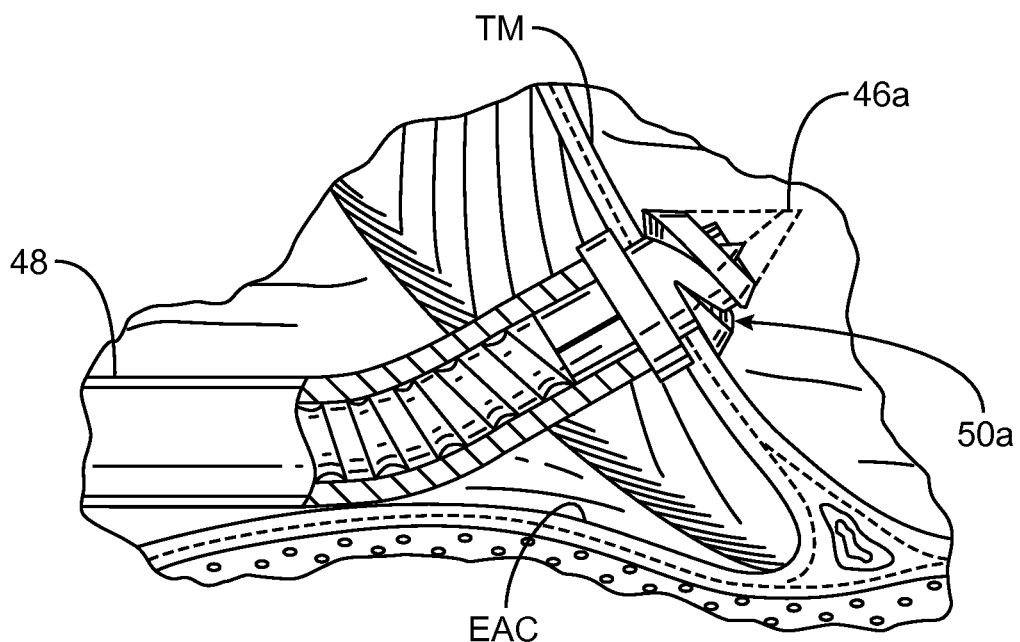

A variety of alternative tympanic tubes and deployment systems might be used with probe assembly 12 in system 10. For example, a tube with helical thread 50a and probe tip 46a are illustrated in FIGS. 8A and B, and are more fully described in U.S. Pat. No. 5,775,336, the full disclosure of which is incorporated herein by reference. In this embodiment a distal portion 80 of tool shaft 48 has a coiled construction to provide lateral flexibility with column strength. Still further alternatives are possible, including a multi-part probe tip 46b which releasably but positively restrains tube 50 in a channel 82, as illustrated in FIGS. 9A-9G. Sequentially sliding individual lateral portions of tip 46b proximally, beginning with a central portion, allows the tip to be removed from within tube 50 without pulling the tube away from the tympanic membrane. Still further alternative tympanic tube structures and deployment probes are possible, including many of those previously proposed or now in commercial use.

Figure 2A:
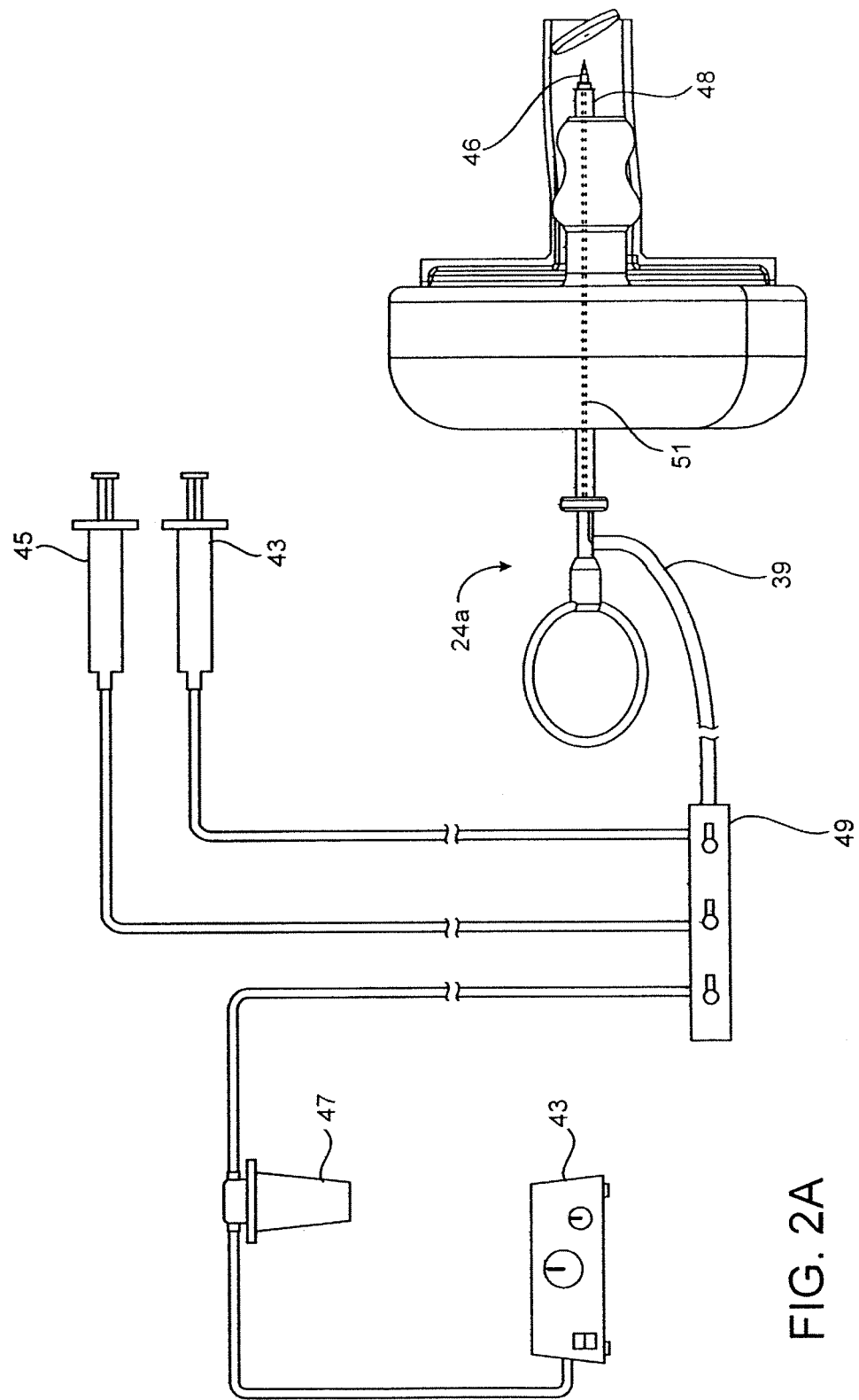
FIGS. 2A and 2B schematically illustrate fluid delivery and/or removal systems of the probe and guide structure, respectively.

Referring now to FIG. 2A, aspiration, irrigation, and local drug delivery proximal and/or distal of the tympanic membrane can be accomplished using a lumen 51 in a probe 24a. The lumen is contained within the treatment probe shaft 48 and has an exit port at the distal membrane piercing tip 46.

Lumen 51 provides a passage for introduction of fluids such as saline for irrigation, a local anesthetic agent to prepare the are for the myringotomy and tympanostomy procedure, and the like, as described above. Fluids may be delivered as a stream or as an atomized mist. Lumen 51 can also be used to aspirate fluids from the external auditory canal, the middle ear, or the like.

Lumen 51 can be coupled to fluid delivery or vacuum aspiration sources by tubing 39. For example, tubing 39 may provide fluid communication between lumen 51 and a source of irrigation fluid, typically a syringe 43. Lumen 51 may similarly be coupled to a source of a drug, preferably an anesthetic agent, typically a syringe 45. Lumen 51 may also be attached to a wall vacuum, a vacuum bottle, a vacuum pump unit 43, or any other vacuum source. This vacuum source may also employ a separate fluid collection chamber 47. The lumen can be attached to a plurality of such components by separate tubing 39, or a single connection to the lumen can be used for a plurality of components using a manifold 49.

Figure 2B:
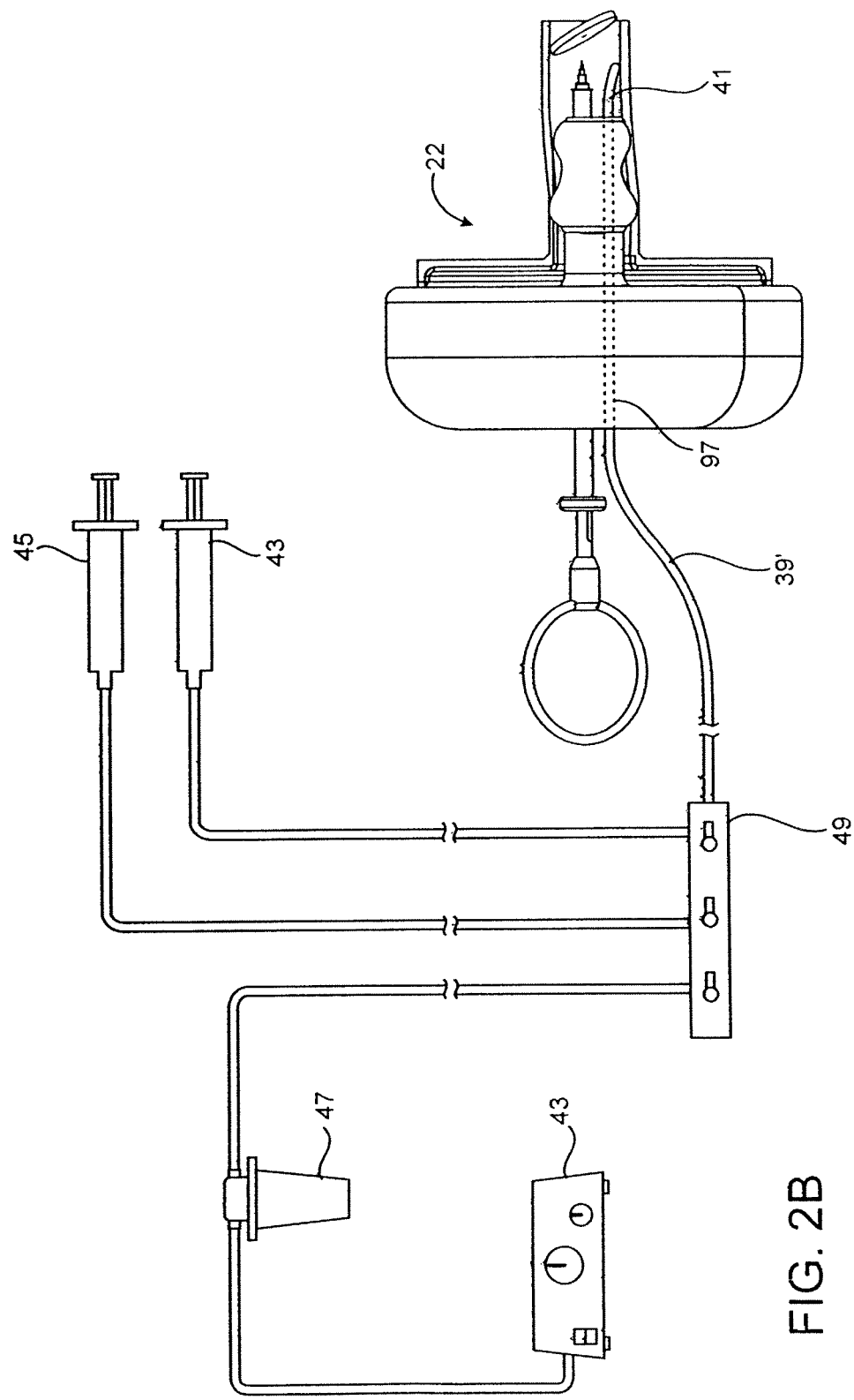

Referring now to FIG. 2B, aspiration, irrigation, local drug delivery, and the like may be provided via lumen 97 in guide structure 22. This lumen may optionally provide passage for introduction of a manipulatable tube 39'. Preferably this tube will have a curved distal portion 41 to facilitate aiming fluid toward a desired area of the external auditory canal for irrigation, aspiration, drug delivery, and the like.

Tube 39' can be coupled to a source of irrigation fluid, typically a syringe 43. It can be coupled to a source of a drug, preferably an anesthetic agent, typically a syringe 45. Tube 39' can also be attached to a wall vacuum, a vacuum bottle, a vacuum pump unit 43, or any other vacuum source. This vacuum source may also employ a separate fluid collection chamber 47. A single tube 39' can be used for a plurality of fluid manipulation components via a manifold 49, or separate tubes can be sequentially deployed through lumen 97.

Figure 10:
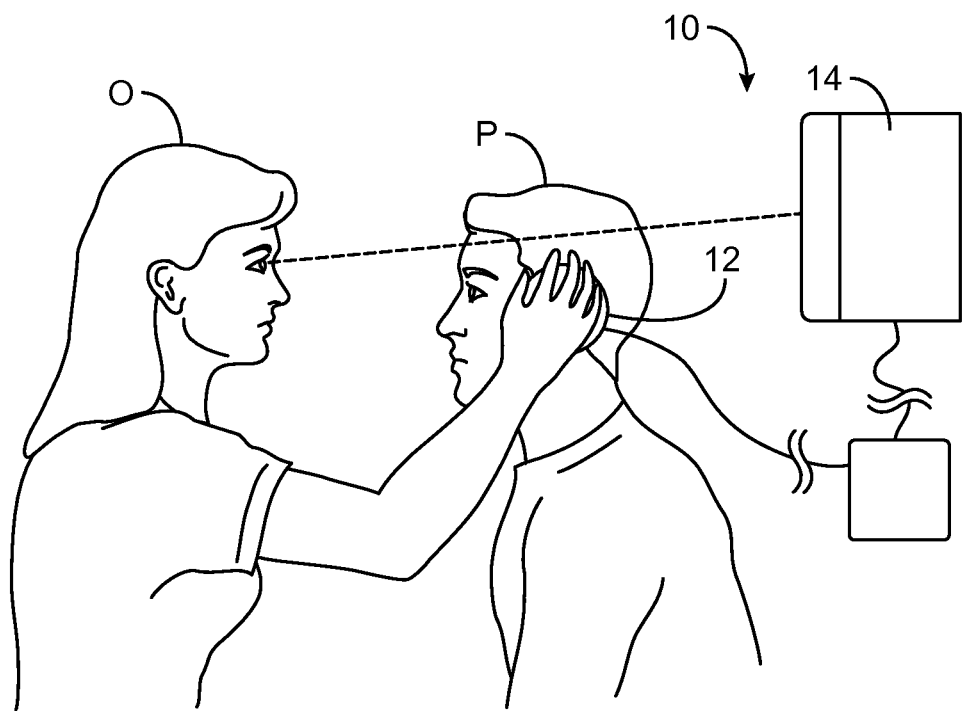
FIG. 10 illustrates a tympanostomy tube treatment procedure according to the principles of the present invention.

Use of system 10 by a system operator O for treatment of a patient P can be understood with reference to FIGS. 10-13E. Patient P will often be a child. Optionally, a mild sedative such as medazolam (Versed) may be given to the patient at the discretion of the system operator, who may optionally be a doctor. A local anesthesia, such as Lidocaine drops, may be placed in the ear (or ears) to be treated. Cerumen may be removed prior to and/or after mounting of the probe assembly. As mentioned above, anesthesia, and other agents may alternatively be dispose on or distributed through guide structure 22 of probe assembly 12. Water or other cerumenolytic agents such as Triethanolamine polypeptide oleatecondensate, hydrogen peroxide, or the like may also be introduced and/or removed via one or more lumen (see lumen 97 of FIG. 3) of the guide structure 22. Preferably, patient P is upright and awake with the system operator disposed in front of the patent, as illustrated in FIG. 10. Operator O will direct the procedure videoscopically with reference to an image 90 shown in viewing monitor 14, which may be placed behind and to the side of patient P.

Figure 13A:
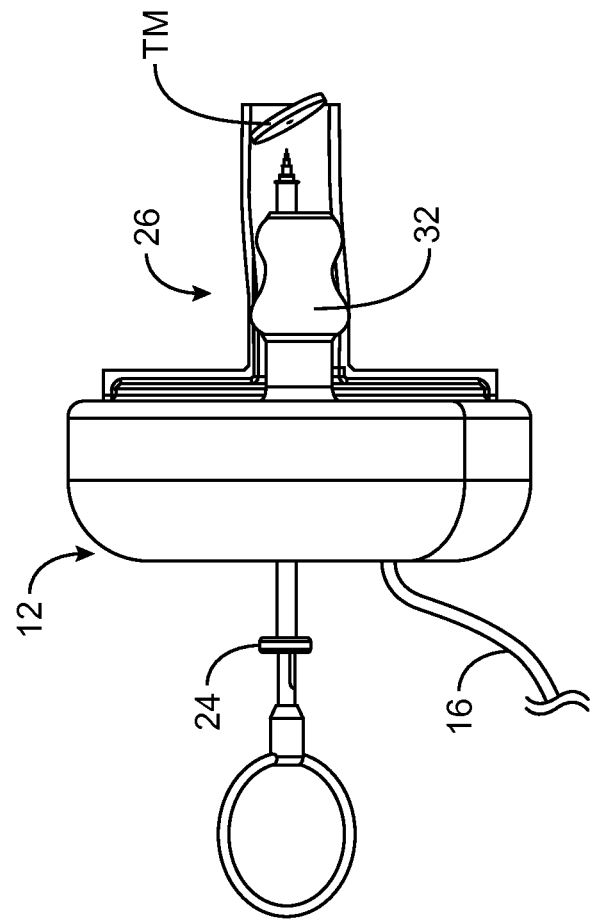
FIGS. 13A-13E schematically illustrate a method for using the guide structure and treatment probe of FIG. 1 to deploy a tympanostomy tube in a target region of a tympanic membrane.
Figure 12:
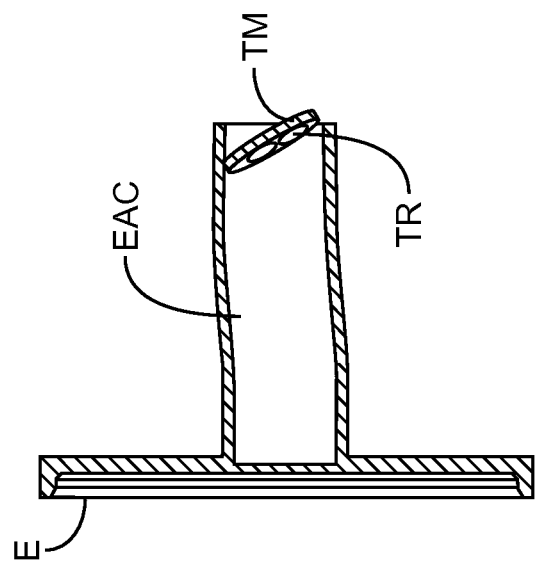
FIG. 12 schematically illustrates a simplified model of an auditory canal.

A simplified model of ear E is shown in FIG. 12, and shows tympanic membrane TM disposed within external auditory canal EAC. A target region TR for deployment of tympanostomy tube 50 may be disposed below a central portion of the membrane occupied by ossicles and other important structures (i.e., nerves and arteries) of the middle ear. As shown in FIG. 13A guide structure 22 is mounted to the ear E by inserting at least a portion of shaft 26 into the external auditory canal EAC. Optionally, probe 24 may be separated from the guide structure during insertion of the shaft, and the inserted portion of the shaft may comprise a deformable structure so as to avoid trauma during insertion. Once shaft 26 is in place, conformable body 32 engages the surrounding tissue surface so as to affix the guide structure. This engagement may result from resilient expansion of a foam of conformable body 32, for example. If probe 24 was not in place during positioning of the shaft it is inserted into probe lumen 42 as seen in FIG. 2.

With shaft 26 in place, operator O can then examine the tympanic membrane TM image shown in monitor 14, as provided by the image capture device of probe assembly 12 (see imaging lens 60 in FIG. 3). Illumination for imaging of the tympanic membrane may be provided by one or more illumination transmitting structure of the probe assembly 12 (see illumination transmitting fibers 58 of FIG. 3).

Figure 11A:
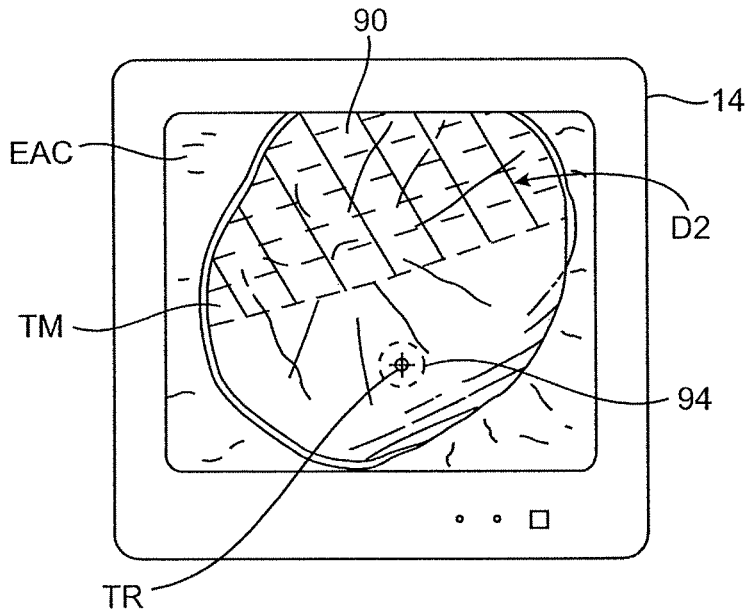
FIG. 11A illustrates a display with a superimposed template for assisting registration.
Figure 11:
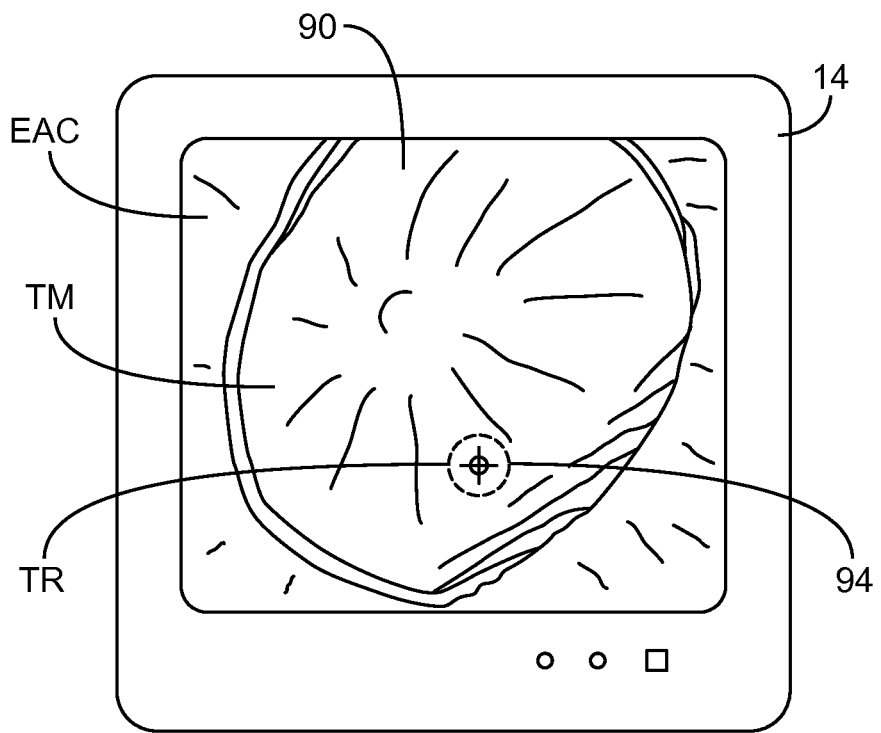
FIG. 11 illustrates a videoscopic image and its use for directing the tympanostomy tube placement procedure of FIG. 10.
Figure 13B:
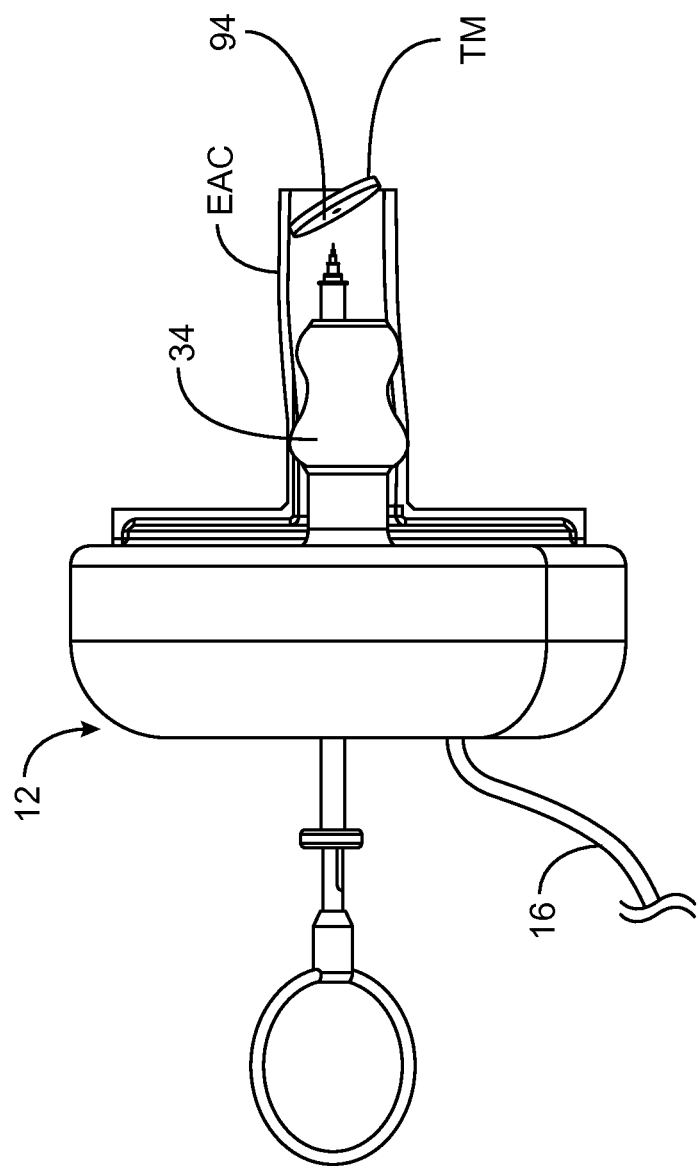

As illustrated in FIGS. 13B and 11, a marker or pointer 94 may be displayed on image 90 as shown to the operator O. The pointer may indicate an alignment of the probe 24 with the target region TR of the tympanic membrane TM, the pointer optionally being generated by transmitting an imagable light beam from the probe assembly onto the membrane with an aiming beam transmitter 62, as described above with reference to FIG. 3. In some embodiments, a reticule or template may be superimposed on the image displayed to the system operator, particularly where the alignment between the image capture device and the treatment probe is fixed. Such a reticule or template may comprise a simple transparent overlay or acetate disposed over the surface of monitor 14. As shown in FIG. 11A, the image may alternatively be evaluated and an overlaying image or template superimposed thereon to indicate a Danger Zone (DZ), the anatomic region in which significant complication may result if the myringotomy with/without tube placement was performed.

Figure 13C:
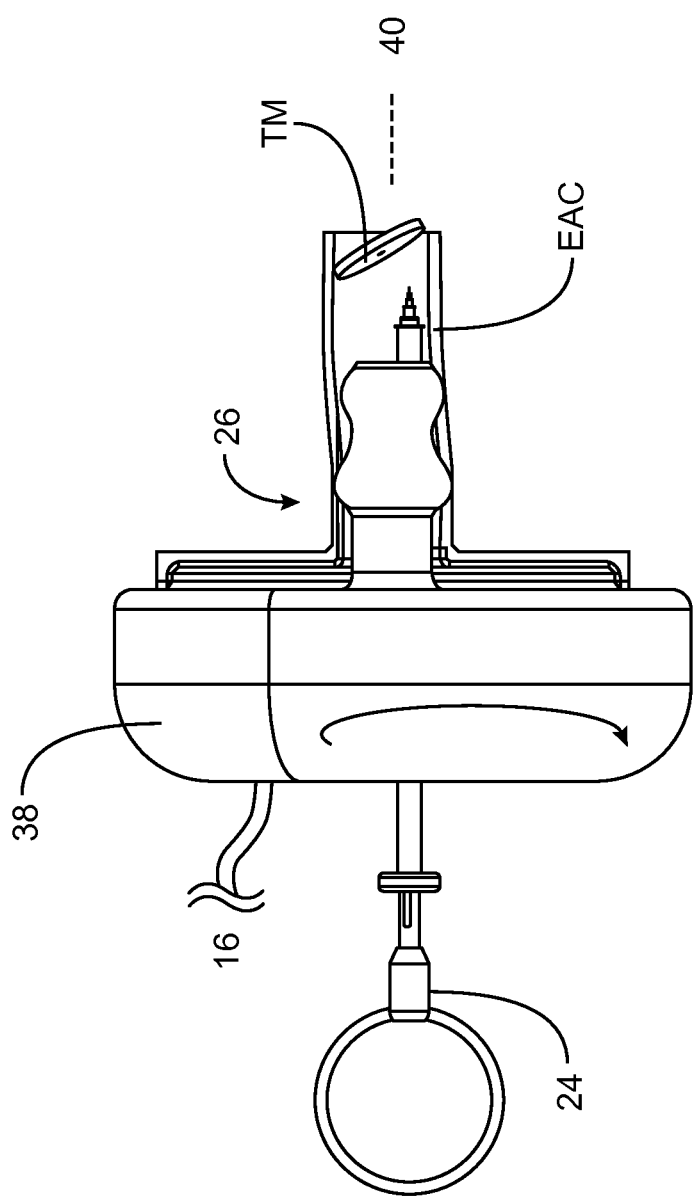

Inner shaft 26 of guide structure 22 (see FIGS. 2 and 4) may be rotated about axis 40, as shown in FIG. 13C, to bring pointer 94 into registration with a target region TR of tympanic membrane TM. As can be understood with reference to FIGS. 10 and 4, this articulation of the guide structure may be accomplished by grasping and turning handle 38 so as to rotate the inner shaft 26 within positioning surface 32. If the image capture device is affixed relative to the inner shaft, the image of the tympanic membrane shown in monitor 14 may rotate during this registration process. Friction of the bearing between the positioning surface and the probe lumen may be sufficient to maintain the orientation of the inner shaft when operator O is not manipulating handle 38. The lumen orientation may also be maintained by gentle pressure of the distal surface of the handle 38 or muff structure against the side of the patients skull.

Figure 13D:
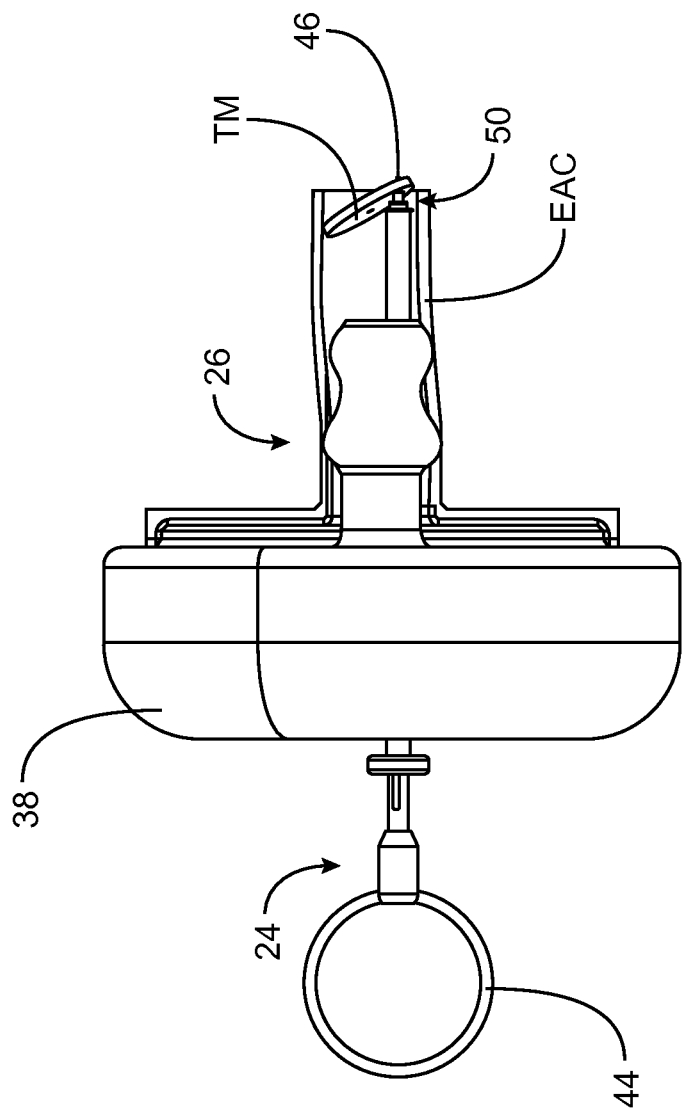

Once treatment probe 24 is properly registered with the target region TR of the tympanic membrane TM as illustrated in FIG. 13C, and once the registration has been verified by determining that the location of pointer 94 is within the target region, treatment is effected by actuating probe actuator 44. Actuator 44 may be advanced distally so that probe tip 46 pierces tympanic membrane TM, as illustrated in FIG. 13D. Inadvertent distal advancement of actuator 34 may be inhibited by detent engagement between probe 24 and the guide structure 22, by a releasable locking mechanism, or the like. The actuation stroke continues so that the distal flange of tympanostomy tube 50 is advanced through the tympanic membrane. The stroke may be terminated when a flange of the probe engages the tympanic membrane, when a limit surface of probe 24 engages a limit surface of the guide structure, or when the system operator visually determines appropriate by reference to monitor 14. Optionally, an aspiration and/or irrigation lumen may have a port in tip 46 of probe 24, so that the probe can be used to drain and/or clear material from the middle ear while extending through tympanic membrane TM. Alternatively, separate fluid clearing and/or tube implanting structures might be supported by guide structure 22.

Figure 13E:
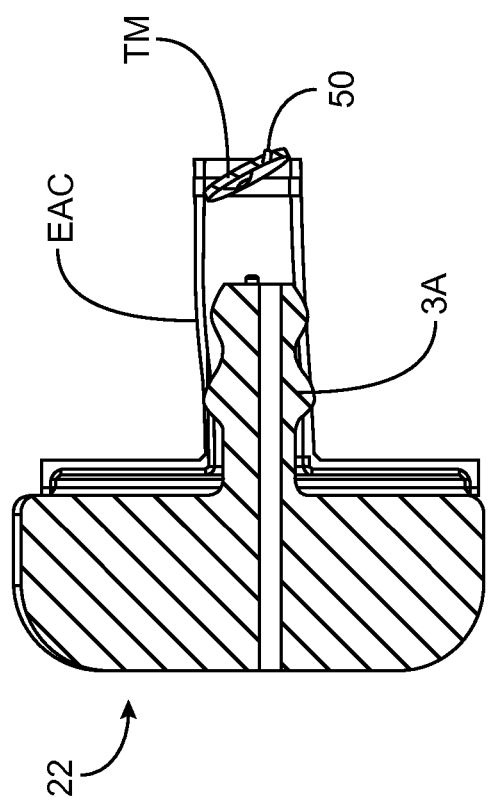

As illustrated in FIG. 13E, treatment probe 24 can be withdrawn proximally from the tympanic membrane. The distal flange of tube 50 should inhibit proximal motion of the tube, so that the tube slides off tip 46 of probe 24. The probe may optionally be withdrawn clear of guide structure 22, as shown, and the imaging system may be used to verify that tympanostomy tube 50 is properly placed.

While the exemplary structure and method have been described in some detail, by way of example and for clarity of understanding, a variety of changes, adaptations, and modifications will be obvious to those of skill in the art. Hence, the scope of the present invention is limited solely by the appended claims.

What is claimed is:

1. A system for treating an ear of a patient having a tympanic membrane and a tissue surface, the system comprising:
    (a) a guide structure, the guide structure having a distal end, a positioning surface and a rotatable shaft including a lumen extending to the distal end, wherein the shaft defines a longitudinal axis, wherein the lumen passes through the shaft along an axis offset from the longitudinal axis of the shaft such that the axis of the lumen is rotatable about the longitudinal axis of the shaft;
    (b) a tympanic membrane treatment probe oriented by the guide structure, wherein the tympanic membrane treatment probe is further supported within the lumen of the guide structure, the treatment probe including a probe lumen extending to the distal end of the guide structure and within the lumen of the guide structure and wherein the guide structure is configured to mechanically register the position of the treatment probe in relation to a target region of the tympanic membrane when the positioning surface engages the tissue surface of the ear, wherein the guide structure is operable to maintain the position of the treatment probe in accordance with the registered position of the treatment probe; and
    (c) a tympanic tube associated with the treatment probe and housed within the probe lumen, wherein the tympanic tube comprises a proximal flange and a distal flange with a tubular body therebetween, the tympanic tube being arranged to be retractable within the probe lumen.

2. The system of claim 1, the tissue surface comprising an auditory canal, wherein the guide structure comprises a conformable body insertable into the auditory canal.

3. The system of claim 2, wherein the shaft is laterally flexible to conform with a bend of the auditory canal during rotation of the shaft.

4. The system of claim 3, wherein the treatment probe conforms with a bend of the auditory canal during rotation of the shaft.

5. The system of claim 2, wherein the conformable body comprises a foam, further comprising an agent disposed on or in the foam, the agent comprising at least one member selected from the group consisting of a local anesthetic agent, an antibacterial agent, an antibiotic agent, and a cerumenolytic agent.

6. The system of claim 2, wherein the conformable body comprises at least one member of the group consisting of a balloon and a solid elastomer.

7. The system of claim 1, further comprising an image capture device supported by the guide structure for imaging the tympanic membrane, the image capture device coupled to a monitor.

8. The system of claim 7, further comprising an illumination source carried by the guide structure for illuminating the tympanic membrane.

9. The system of claim 1, further comprising a light transmitter directing a light beam distally, the beam aligned with the treatment probe to verifying registration of the treatment probe with the target region.

10. The system of claim 1, wherein the treatment probe comprises a probe shaft disposed in the lumen of the guide structure, the probe shaft coupled to an actuator accessible when the positioning surface engages the tissue surface, the probe shaft advancing coaxially with the lumen in response to the actuator.

11. The system of claim 10, wherein the treatment probe has a distal tip for piercing the tympanic membrane.

12. The system of claim 11, wherein the distal tip comprises a surgically sharp distal edge.

13. The system of claim 11, wherein the tympanic tube is releasably carried on the probe shaft proximally of the tip.

14. The system of claim 13, wherein a distal surface of the distal tip is contiguous with a distal surface of the tympanic tube.

15. The system of claim 13, the tubular body having an elongate opening with a first cross-sectional dimension and a second cross-sectional dimension greater than the first, the tip of the probe shaft having a distally oriented edge oriented along a height, the distal surface of the distal flange of the tympanic tube angling proximally and radially outwardly.

16. The system of claim 10, wherein a limit surface of the treatment probe inhibits axial movement of the shaft after the probe pierces the tympanic membrane.

17. The system of claim 10, wherein a limit surface inhibits advancement of a proximal flange of the tympanostomy tube into a middle ear.

18. The system of claim 10, wherein the lumen is selectively repositionable relative to the positioning surface for selective registration of the treatment probe with the target region.

19. The system of claim 1, the guide structure further comprising a proximal body having a distal surface oriented toward an external ear of the patient and an exposed proximal surface, the proximal body comprising a muff manipulatable by a system operator to position the guide structure and register the treatment probe with the target region under remote imaging, the muff inhibiting direct optical visualization of the tympanic membrane.

* * * * *